United States Patent [19]

Suzuki

[11] 4,327,038
[45] Apr. 27, 1982

[54] METHOD FOR PREPARING OPTICALLY ACTIVE 2,2-DIMETHYL-3-(2,2-DICHLOROVINYL)-CYCLOPROPANECARBOXYLIC ACID

[75] Inventor: Yukio Suzuki, Toyonaka, Japan

[73] Assignee: Sumitomo Chemical Company, Limited, Osaka, Japan

[21] Appl. No.: 225,750

[22] Filed: Jan. 16, 1981

[30] Foreign Application Priority Data

Jan. 31, 1980 [JP] Japan ................................. 55-11313

[51] Int. Cl.³ ...................... C07C 61/04; C07B 19/00
[52] U.S. Cl. ............................... 260/501.16; 562/401
[58] Field of Search .................... 562/401; 260/501.16

[56] References Cited

U.S. PATENT DOCUMENTS

| | | | |
|---|---|---|---|
| 3,646,118 | 2/1972 | Goffinet et al. ..................... | 562/401 |
| 3,739,019 | 6/1973 | Ueda et al. ........................... | 562/401 |
| 3,842,125 | 10/1974 | Horiuchi et al. .................... | 562/401 |
| 3,879,451 | 4/1975 | Yoshioka et al. ................... | 562/401 |
| 4,236,026 | 11/1980 | Naumann ............................ | 562/401 |

FOREIGN PATENT DOCUMENTS

| | | |
|---|---|---|
| 2427321 | 5/1979 | France . |
| 51-36441 | 3/1976 | Japan . |
| 51-143647 | 12/1976 | Japan . |
| 53-46835 | 12/1978 | Japan . |
| 54-73758 | 6/1979 | Japan . |

OTHER PUBLICATIONS

Nature, 244, pp. 456–457 (1973), "Potent Pyrethroid Insecticides from Modified Cyclopropane Acids".
Pestic. Sci., 5, pp. 791–799 (1974), "The Pyrethrins and Related Compounds", Paul E. Burt et al.
Eliel; Stereochemistry of Carbon Compounds, 47–83 (1962) (Published by McGraw-Hill Book Co., Inc. (N.Y.)).

*Primary Examiner*—Natalie Trousof
*Assistant Examiner*—Vera C. Clarke
*Attorney, Agent, or Firm*—Stevens, Davis, Miller & Mosher

[57] ABSTRACT

A method for preparing (1R,cis)-2,2-dimethyl-3-(2,2-dichlorovinyl)cyclopropanecarboxylic acid useful as an acid part of practically effective insecticidal esters, which comprises reacting 2,2-dimethyl-3-(2,2-dichlorovinyl)cyclopropanecarboxylic acid containing 70% or more of the cis-form with an equimolar or less amount of (+)-1-phenyl-2-(p-tolyl)ethylamine, allowing a diastereomer salt to precipitate from a solvent, then, if necessary, purifying said salt, and decomposing said salt with a base or an acid to yield (1R,cis)-2,2-dimethyl-3-(2,2-dichlorovinyl)cyclopropanecarboxylic acid.

7 Claims, No Drawings

METHOD FOR PREPARING OPTICALLY ACTIVE 2,2-DIMETHYL-3-(2,2-DICHLOROVINYL)CYCLO-PROPANECARBOXYLIC ACID

This invention relates to a method for the optical resolution of cis-2,2-dimethyl-3-(2,2-dichlorovinyl)cyclopropanecarboxylic acid [hereinafter 2,2-dimethyl-3-(2,2-dichlorovinyl)cyclopropanecarboxylic acid is referred to briefly as DV acid].

DV acid is the acid part of the molecules of Cypermethrin and Permethrin which have recently attracted keen attention as an agricultural insecticide or a disinfectant insecticide. Since DV acid has two asymmetric carbon atoms in its cyclopropane ring, it has four stereoisomers. Of the four stereoisomers of Permethrin and Cypermethrin, those having an acid part in (1S, cis)- or (1S, trans)-form possess little insecticidal activity, whereas, in practice, those esters which have an acid part in (1R, cis)- or (1R, trans)-form are effective. Although the insecticdal activity difference between the (1R, cis)-form ester and the (1R, trans)-form ester depends on the target insect species, the former ester shows a higher activity against principal agricultural pests.

For the synthesis of (1R, cis)-DV acid there has heretofore been known a method in which said acid is derived from optically active chrysanthemic acid [M. Elliott et al., Nature, 244, 456 (1973)]. This method, however, uses a starting material which is expensive or is difficultly available on commercial basis, and involves many preparative steps, resulting in a low yield of the intended product.

There is also known a method for synthesizing DV acid rich in (1R, cis)-form by use of an asymmetric copper catalyst (Japanese Patent Publication No. 46,835/1978). One of the disadvantages of this method is that a number of steps are involved in preparing the catalyst.

On the other hand, there are known preparative methods for DV acid by the optical resolution. Firstly, as to trans-DV acid, the known optical resolution method employs D-(−)-threo-1-p-nitrophenyl-2-(N,N-dimethylamino)-propane-1,3-diol, (+)-erythro-1,2-diphenyl-2-hydroxyethylamine and (−)-β-dimethylamino-α,α-dimethyl-β-phenethyl alcohol (P. E. Burt et al., Pestic. Sci., 1974, 5, 791–799; Japanese Patent Application Laid-open Nos. 36,441/1976 and 143,647/1976).

Secondly, as to cis-DV acid, there are known optical resolution method which employs (+)-α-methylbenzylamine and (−)-quinine (P. E. Burt et al., loc. cit.; British Patent Application 2008589A). In the former case, because of low optical purity of the resulting (1R, cis)-DV acid, recrystallization of the (+)-α-methylbenzylamine salt must be repeated several times and also the method lacks reproducibility. In the latter case, being one of the natural alkaloids, the (−)-quinine is unstable in its commercial supply and demand, lacks in the chemical stability which is necessary for its recovery and reuse in the cycle of industrial process, and has, above all, a great disadvantage of a much higher price compared with synthetic optical resolution agents.

Under the circumstances as described above, the present inventor made extensive studies on the method for optical resolution of cis-DV acid and, as a result, found that optically active 1-phenyl-2-(p-tolyl)ethylamine (hereinafter referred to as PTE), which is one of the most easily available among many synthetic amines which are optically active, may be used industrially as an optical resolution agent for the cis-DV acid. Further investigations based on this finding have led to the accomplishment of this invention.

Thus, the present invention provides a method for obtaining (1R,cis)-DV acid by adding to a DV acid containing 70% or more of the cis-form (+)-PTE in an equimolar or less amount of said DV acid, allowing a diastereomer salt to deposit from a solvent, then, if necessary, purifying said salt, and decomposing said salt with a base or an acid to set free the (1R,cis)-DV acid. As a matter of course, in this case, (1S, cis)-DV acid can be obtained when (−)-PTE is used instead of the (+)-PTE.

The method of this invention is described in detail below.

At first, to a DV acid containing 70% or more of the cis-form, is added (+)-PTE in an equimolar or less amount of said acid in order to form a salt. The use of the amine in an amount more than equimolar amount of the acid will cause a decrease in optical purity of the DV acid in the salt. In view of the optical purity and yield of the salt, the amount added of (+)-PTE is preferably in the range of from 0.5 to 0.8 mole and its optical purity is preferably 90% or higher, though higher the better.

The DV acid used as starting material should contain 70% or more, preferably 80% or more, of the cis-form, though higher the better.

The salt formation is carried out preferably in a solvent. It is also possible to carry out in the presence of other achiral organic or inorganic base in an amount of 0.5 mole or less per mole of the DV acid used as starting material.

The solvent may be freely selected from inert solvents other than those acidic or basic solvents which interfere with the salt formation.

Then, thus formed salt is allowed to precipitate in the solvent to separate the crystals from the mother liquor. In this case, heating is not essential but it is general that the temperature of the solution is raised before or after the salt formation and then cooled to a temperature at which the salt crystals fully precipitate to separate the crystals from the mother liquor. In this case, the solvent may be freely selected from inert solvents other than those acidic or basic solvents which interfere with the salt formation. In view of handling, a lower alcohol or a mixture of a lower alcohol and water is preferred.

If necessary, the salt thus formed can be improved in optical purity or chemical purity by recrystallization or the like treatment using a solvent which may be the same as or different from that used in depositing the salt.

The salt isolated as crystals is again separated into DV acid and PTE by the action of an acid or a base. The acid to be used in this case should be an acid such as, for example, a mineral acid (e.g. hydrochloric acid, sulfuric acid) which is stronger than the DV acid, and the base to be used in this case should be a base such as, for example, an inorganic base (e.g. sodium hydroxide, potassium hydroxide) which is a stronger base compared with the PTE. Such an acid or a base is used in an equimolar or more amount of the salt. Since the solubility of an inorganic acid salt of PTE in water is small, it is preferable to decompose at first the salt with an inorganic base and, after removing the PTE by extraction with an organic solvent, to set free the DV acid with an excess of an inorganic acid and recover it. When the DV acid containing trans-body is used as a starting material in the method of this invention, the DV acid to be obtained contains some amount of the trans-body which can be removed, if necessary, by recrystallization process in the form of the intermediate DV acid salt or the separated free DV acid.

The invention is illustrated below with reference to Examples and Comparative Examples, in which "cis-DV acid" and "trans-DV acid" are those containing substantially no other isomers; and the optical purity or the optical isomer ratio was determined by converting the DV acid into a d-2-octanol ester and analyzing the gas chromatography [M. Horiba et al., Agr. Biol. Chem., 41, 581 (1977)].

EXAMPLE 1

To a solution of 10.45 g (50 mmoles) of cis-DV acid in 70 g of ethanol, while refluxing, was added dropwise 6.87 g (32.5 mmoles) of (+)-PTE. Upon cooling slowly to about 60° C., crystals were deposited. After cooling down to 26° C., the crystals were collected by filtration and washed with 50 g of ethanol. The yield of crystals was 7.59 g (72.2% based on one-half the charged DV acid); $[\alpha]_D^{21}$ +39.8° (methanol, c=1.07); melting pint 156°–159°C.

A 7 g portion of the crystals was added to a mixture of 20 cc of toluene and 50 cc of a 2% solution of sodium hydroxide. The resulting mixture was stirred for one hour at 40° C. and allowed to settle into two layers. The aqueous layer was thoroughly mixed with 10 cc of toluene and allowed to settle into two layers. The aqueous layer was thoroughly mixed with 10 cc of 10% hydrochloric acid and 20 cc of toluene and allowed to settle into two layers. The aqueous layer was extracted with 20 cc of toluene. The toluene layers were combined, washed with water and concentrated to obtain 3.45 g of (1R, cis)-DV acid; $[\alpha]_D^{24.5}$+31.86° (chloroform, c=3.44); optical purity 90.0%.

EXAMPLE 2

To a solution of 10.45 g (50 mmoles) of cis-DV acid in 51 g of 80% ethanol, was added dropwise at 20° to 30° C. 6.87 g (32.5 mmoles) of (+)-PTE. The reaction system became a highly viscous slurry. After complete dissolution by heating, the resulting solution was cooled slowly with stirring (deposition of crystals at about 58° C.) and the crystals were collected by filtration at 23° C. The crystals were washed with 60 cc of 80% ethanol and dried to obtain 8.73 g (83.2% based one one-half the charged DV acid) of the intended salt which was subsequently decomposed as in Example 1 to obtain (1R, cis)-DV acid, $[\alpha]_D^{23}$+24.2° (chloroform, c=4.16).

EXAMPLE 3

To a solution of 10.45 g (50 mmoles) of cis-DV acid in 73.15 g of ethanol, while being refluxed, was added dropwise 8.45 g (40 mmoles) of (+)-PTE. The solution was slowly cooled (deposition of crystals at about 56° C.) and stirred at 21.5° C. for 90 minutes. The crystals were collected by filtration, washed with 150 cc of ethanol, and dried to obtain 8.46 g (80.9% based on one-half the charged DV acid) of the intended salt which was then decomposed to yield (1R, cis)-DV acid. $[\alpha]_D^{24}$+24.7° (chloroform, c=3.44).

EXAMPLE 4

To a solution of 10.45 g (50 mmoles) of cis-DV acid in 52.25 g of methanol, while being refluxed, was added dropwise 5.56 g (25 mmoles) of (+)-PTE. After completion of the dropwise addition, the reaction solution was slowly cooled (deposition of crystals at about 47° C.) and filtered at 23° C. to collect the crystals. The crystals were washed with 20 cc of methanol and dried to obtain 5.38 g (51.5% based on one-half the charged DV acid) of the intended salt which on decomposition yielded (1R, cis)-DV acid, $[\alpha]_D^{24}$+28.7° (chloroform, c=4.41).

EXAMPLE 5

To a solution of 10.45 g (50 mmoles) of cis-DV acid in 52.25 g of carbon tetrachloride, while being refluxed, was added dropwise 5.56 g of (+)-PTE. After completion of the addition the reaction solution was cooled slowly (deposition of crystals at about 65° C.), stirred at 55° C. for one hour, and filtered at the same temperature. The salt was washed with 30 cc of carbon tetrachloride and dried to obtain 6.24 g (59.4% based on one-half the charged DV acid) of the salt which yielded (1R, cis)-DV acid, $[\alpha]_D^{23}$+15.1° (chloroform, c=6.0).

EXAMPLE 6

Into 137.8 g of ethanol, was added 24.35 g of a salt of crude (1R, cis)-DV acid {$[\alpha]_D^{23}$+24.58° (chloroform, c=3.10); 72.5% optical purity} and (+)-PTE, and then the salt was dissolved under reflux. The resulting solution was slowly cooled with stirring (deposition of crystals at about 71° C.) and filtered at 27° C. The crystals were washed with 50 g of 60% ethanol, and dried to obtain 19.37 g (79.5% recrystallization yield) of crystals which yielded (1R, cis)-DV acid having an optical rotation $[\alpha]_D^{22.5}$ of +33.0° (chloroform, c=3.77) and an optical purity of 97.4%.

EXAMPLE 7

To a solution of 10.46 g (50 mmoles) of DV-acid containing the cis-form and trans-form in a ratio of 80:20 in 73.22 g of ethanol, was added dropwise at 22° to 25° C. 6.87 g of (+)-PTE. After completion of the addition, the solution was stirred continually at 25° C. to deposit crystals gradually. After 3 hours of stirring, the mixture was filtered and the salt was washed with 30 cc of ethanol and dried to obtain 4.20 g (40.0% based on one-half the charged DV-acid) of the salt which yielded DV acid of the following analysis: 87.2% (1R, cis); 5.5% (1S, cis); 2.4% (1R, trans); 4.9% (1S, trans); $[\alpha]_D^{21}$+26.5° (chloroform, c=2.04).

EXAMPLE 8

To a solution of 10.46 g (50 mmoles) of DV acid containing the cis-form and trans-form in a ratio of 80:20 in 73.22 g of 80% ethanol, was added dropwise at room temperature 6.87 g of (+)-PTE. After completion of the addition, the precipitated crystals were dissolved by elevating the temperature and the solution was then cooled with stirring (deposition of crystals at 42° C.). The crystals were collected by filtration at 23° C., washed with 30 cc of 80% ethanol, and dried to obtain 7.15 g (68.0% based on one-half the charged DV acid) of the salt having a melting point of 145°–152° C. and an optical rotation $[\alpha]_D^{21}$ of +44.4° (methanol, c=1.76). The DV acid obtained from the salt showed the following analysis: 79.0% (1R, cis); 11.7% (1S, cis); 3.9% (1R, trans); 5.9% (1S, trans); $[\alpha]_D^{21}$ +24.2° (chloroform, c=2.06).

EXAMPLE 9

To a solution of 10.46 g (50 mmoles) of DV acid containing the cis-form and trans-form in a ratio of 70:30 in 73.22 g of ethanol, was added dropwise at room temperature 6.87 g of (+)-PTE. After completion of the addition, the mixture was cooled with stirring to 5° to 7° C. when crystals separated out. The mixture was stirred for further four hours and filtered. The crystals were washed with 30 cc of ethanol and dried to obtain 4.43 g (42.2% based on one-half the charged DV acid) of the salt. The DV acid obtained from the salt showed the following analysis: 47.4% (1R, cis); 29.3% (1S, cis); 13.0% (1R, trans); 10.3% (1S, trans); $[\alpha]_D^{21} + 8.64°$ (chloroform, c=2.08).

COMPARATIVE EXAMPLE 1

To a solution of 14.6 g (70 mmoles) of cis-DV acid in 250 cc of benzene, while being refluxed, was added dropwise 8.47 g (70 mmoles) of (+)-α-methylbenzylamine. After completion of the addition, the mixture was cooled with stirring (deposition of crystals at 43° C.) and filtered at 20° C. The crystals were washed with 30 cc of benzene to obtain 21.47 g (93.1% based on the charged DV acid) of crystals. The cis-DV acid obtained by the decomposition of above crystals showed an optical rotation $[\alpha]_D^{24}$ of −0.62° (chloroform, c=5.78).

COMPARATIVE EXAMPLE 2

To a solution of 2.67 g (12.8 mmoles) of cis-DV acid in 45.7 cc of benzene, while being kept at 50° C., was added dropwise 1.55 g (12.8 mmoles) of (+)-α-methylbenzylamine. After addition of 35.5 cc of benzene, the reaction mixture was left standing at 50° to 60° C. for 2 hours, then at room temperature overnight, and filtered at 25° C. The crystals were washed with 10 cc of benzene to obtain 3.84 g (91.1% based on the charged DV acid) of crystals. The cis-DV acid obtained by the decomposition of said crystals showed an optical rotation $[\alpha]_D^{25}$ of −0.58° (chloroform, c=5.53).

COMPARATIVE EXAMPLE 3

To a solution of 10.45 g (50 mmoles) of cis-DV acid in 52 g of 80% ethanol, was added dropwise at 20° to 25° C. 5.56 g (32.5 mmoles) of (−)-α-(1-naphthyl)-ethylamine. After completion of the addition, crystals separated out, forming a viscous slurry which changed into a clear solution upon heating to 45° C. The solution was cooled slowly (deposition of crystals at 36° C.) and filtered at 23.5° C. The crystals were washed with 50 cc of 80% ethanol and dried to obtain 5.59 g (29.4% based on the charged DV acid) of a salt. The cis-DV acid in the salt showed an optical rotation $[\alpha]_D^{23}$ of −1.46° (chloroform, c=5.56).

COMPARATIVE EXAMPLE 4

Optical resolution was performed in the same manner as in Example 2, except that trans-DV acid was used in place of the cis-DV acid. There were obtained 7.81 g (37.2% based on the charged DV acid) of a salt. The trans-DV acid obtained from the salt showed an optical rotation $[\alpha]_D^{23.5}$ of 0.77° (chloroform, c=4.73).

COMPARATIVE EXAMPLE 5

To a solution of 10.46 g (50 mmoles) of DV acid containing the cis-form and trans-form in a ratio of 43.4:56.6 in 73.22 g of ethanol, was added dropwise at room temperature 6.87 g (32.5 mmoles) of (+)-PTE. No crystallization was caused to take place by stirring the solution or by the further dropwise addition of 3.70 g (17.5 mmoles) of (+)-PTE. When 18.3 g of water was added, crystals separated out. The temperature was elevated to 38° C. to dissolve the crystals and the resulting solution was then cooled slowly with stirring (deposition of crystals at 34° C.) and filtered at 25° C. The crystals were washed with 30 cc of ethanol and dried to obtain 9.14 g (43.5% based on the charged DV acid) of a salt. The DV acid obtained from the salt showed the following analysis: 19.9% (1R, cis); 15.3% (1S, cis); 33.3% (1R, trans); 31.5% (1S, trans); $[\alpha]_D^{21} + 0.72°$ (chloroform, c=1.67).

What is claimed is:

1. A method for preparing (1R, cis)-2,2-dimethyl-3-(2,2-dichlorovinyl)cyclopropanecarboxylic acid, which comprises reacting 2,2-dimethyl-3-(2,2-dichlorovinyl)-cyclopropanecarboxylic acid containing 70% or more of the cis-form with an equimolar or less amount of (+)-1-phenyl-2-(p-tolyl)ethylamine, allowing a (1R, cis)-2,2-dimethyl-3-(2,2-dichlorovinyl)cyclopropanecarboxylic acid salt of (+)-1-phenyl-2-(p-tolyl)ethylamine to precipitate from a solvent, and then decomposing the resulting precipitated salt with a base or an acid to yield (1R, cis)-2,2-dimethyl-3-(2,2-dichlorovinyl)-cyclopropanecarboxylic acid.

2. A method according to claim 1, wherein 2,2-dimethyl-3-(2,2-dichlorovinyl)cyclopropanecarboxylic acid containing 80% or more of the cis-form is used.

3. A method according to claim 1, wherein 0.5 to 0.8 mole of the (+)-1-phenyl-2-(p-tolyl)ethylamine is added to 1 mole of cis-2,2-dimethyl-3-(2,2-dichlorovinyl)cyclopropanecarboxylic acid.

4. A method according to claim 1, wherein the reaction of 2,2-dimethyl-3-(2,2-dichlorovinyl)cyclopropanecarboxylic acicd with (+)-1-phenyl-2-(p-tolyl)-ethylamine, and the precipitation of the (1R, cis)-2,2-dimethyl-3-(2,2-dichlorovinyl)cyclopropanecarboxylic acid salt of (+)-1-phenyl-2-(p-tolyl)ethylamine are carried out in the same solvent.

5. A method according to claim 1, wherein the lower alcohol is methanol or ethanol.

6. A method according to claim 1, wherein the purification of the precipitated (1R, cis)-2,2-dimethyl-3-(2,2-dichlorovinyl)cyclopropanecarboxylic acid salt of (+)-1-phenyl-2-(p-tolyl)ethylamine is carried out by recrystallization and then decomposing the said salt with a base or an acid to yield (1R, cis)-2,2-dimethyl-3-(2,2-dichlorovinyl)cyclopropanecarboxylic acid.

7. (+)-1-Phenyl-2-(p-tolyl)ethylammonium (1R, cis)-2,2-dimethyl-3-(2,2-dichlorovinyl)cyclopropanecarboxylate.

* * * * *